United States Patent [19]

Arkles

[11] 4,362,884

[45] Dec. 7, 1982

[54] SILACROWN ETHERS, METHOD OF MAKING SAME, AND USE AS PHASE-TRANSFER CATALYSTS

[75] Inventor: Barry C. Arkles, Oreland, Pa.

[73] Assignee: Petrarch Systems, Inc., Levittown, Pa.

[21] Appl. No.: 323,629

[22] Filed: Nov. 23, 1981

[51] Int. Cl.³ .............................. C07F 7/08; C07F 7/18
[52] U.S. Cl. .................................... 556/446; 260/464; 560/236; 570/143; 570/145; 570/191; 570/196; 570/197; 570/261
[58] Field of Search ......................................... 556/446

[56] References Cited

U.S. PATENT DOCUMENTS

| | | | |
|---|---|---|---|
| 3,078,293 | 2/1963 | Ender | 556/446 |
| 3,475,478 | 10/1969 | Simmler | 556/446 X |
| 3,505,380 | 4/1970 | Berger | 556/446 |
| 3,539,610 | 11/1970 | Berger | 536/446 X |
| 3,987,061 | 10/1976 | Pedersen | 556/446 X |
| 4,098,808 | 7/1978 | Wolfers et al. | 556/446 |

OTHER PUBLICATIONS

C. J. Pederson, *J. Am. Chem. Soc.*, 89, 7017, (1967).
R. Kieble, C. Burkhard, *J. Am. Chem. Soc.*, 69, 2689, (1947).

*Primary Examiner*—Paul F. Shaver
*Attorney, Agent, or Firm*—Seidel, Gonda, Goldhammer & Panitch

[57] ABSTRACT

Organosilicon compounds referred to as silacrown ethers or "silacrowns" are of the general formula:

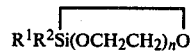

where $R^1$ and $R^2$ are organic radicals or hydrogen and n is an integer between 4 and 10 inclusive. Silacrown ethers are prepared by reacting polyethylene glycol with substituted silanes under conditions promoting cyclization over polymerization. Silacrown ethers may be employed as phase-transfer catalysts in solution or immobilized on siliceous supports.

12 Claims, No Drawings

SILACROWN ETHERS, METHOD OF MAKING SAME, AND USE AS PHASE-TRANSFER CATALYSTS

BACKGROUND OF THE INVENTION

The present invention is directed to the preparation of "silacrowns" or "silacrown ethers"—macrocyclic multidentate ethers which resemble in structure and complexation properties a class of compounds known as "crown ethers", but differ in the replacement of a —$C_2H_4$— group by a silicon group.

Since 1967 when C. Pedersen discovered the crown ethers, literally thousands of applications have developed in which their ability to complex metal ions, solvate inorganic and organic salts in polar and non-polar solvents, and facilitate anionic reactions have been exploited. Much of this work has been reviewed in *Synthetic Multidentate Macrocyclic Compounds* by R. Izatt and J. Christiansen, Academic Press 1978. Two obstacles have prevented their wider utilization, particularly in commercial processes: current synthetic methods are extremely costly, and the materials have generally high levels of toxicity. These factors, coupled with the difficulty in separating the crown ethers during preparation by processes other than distillation, have hindered wider applications. An example is the acylation step in penicillin synthesis.

Although cyclic polyethyleneoxysilanes have been previously reported, the ring structures have fewer members than the silacrowns. The inside diameters of the ring structures are clearly smaller than lithium ions. R. Kieble, C. Burkhard, *J. Am. Chem. Soc.* 69, 2689 (1947). Because the ring structures are so small, these compounds cannot form complexes with cations.

SUMMARY OF THE INVENTION

Silacrowns are macrocyclic multidentate ethers of the general structure:

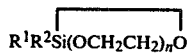

where n is an integer from 4 to 10 inclusive, and $R^1$ and $R^2$ are generally organic radicals such as alkyl, unsaturated alkyl, alkoxy and aryl. Other organic radicals may also be substituted. $R^1$ or $R^2$ may be hydrogen.

Silacrowns are produced by reacting a polyethyleneglycol having the general formula:

where n is an integer between 4 and 10 inclusive, with a silane having the general formula:

under conditions promoting cyclization over polymerization, wherein Y is selected from the group consisting of alkoxy, acyloxy, amino and chloro, and $R^1$ and $R^2$ are alkyl, unsaturated alkyl, alkoxy or aryl. Other organic radicals may also be substituted for $R^1$ and $R^2$. $R^1$ or $R^2$ may be hydrogen.

Silacrowns may be used to catalyze anionic displacement reactions. Immobilized silacrowns formed by the reaction of siliceous materials and silacrown ethers may be used to catalyze liquid/liquid phase transfer.

DETAILED DESCRIPTION OF THE INVENTION

Silacrowns exhibit complexation properties remarkably similar to crown ethers. A specific example is dimethylsila-14-crown-5.

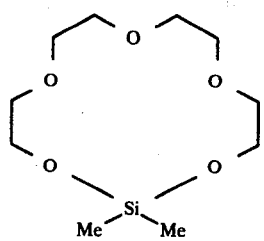

FIG. 1

The name indicates the substituents on silicon, the number of members in the ring, and the number of oxygens. This compound may be compared to the corresponding crown ether, 15-crown-5. Although there is one less member in the ring for the silacrown, the longer silicon-oxygen bonds result in an O-Si-O unit that has 75 percent of the bond length of an O-$CH_2$-$CH_2$-O unit. Simple addition of bond lengths indicates an overall reduction in macrocycle circumference of 4.5 percent when compared to 15-crown-5.

Hereinafter, the absence of a prefix in a silacrown name indicates "dimethyl". Thus, dimethylsila-14-crown-5 may be abbreviated sila-14-crown-5.

The silacrowns are generally colorless, odorless liquids of moderate viscosity. They appear to have the ability to form stable molecular complexes with alkaline or alkaline earth salts in solution as well as in the solid state, behaving as phase transfer catalysts. Solvation of the metal ions leaves anions unencumbered, enabling them to act as potent bases and nucleophiles. This is demonstrated in a number of processes including nitrile, acetate, nitrite, fluoride and iodide displacements. Oxidations with permanganate and chromate are facilitated.

Certain silacrowns have the ability to react with siliceous materials, forming immobilized silacrowns. The immobilized silacrowns demonstrate the same ability to catalyze reactions as their unbound counterparts. They are particularly useful in liquid/liquid phase transfer reactions.

The silicrowns are readily prepared by transesterification of alkoxysilanes with polyethylene glycols.

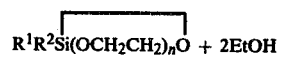

Reaction conditions must be selected to promote cyclization in preference to polymerization. The reaction may be catalyzed by a variety of transesterification catalysts including methylsulfonic acid, toluenesulfonic acid, sodium, titanates and a variety of other materials known in the literature. Titanates are generally preferred. The reactants are combined and approximately 80–95 percent of the alcohol by-product is slowly distilled from the reaction mixture. If the silacrown being prepared contains a moiety which does not have great thermal stability, such as a vinyl group, it is useful to add a higher boiling solvent such as toluene.

The silacrown is removed from the reaction mixture by distillation, shifting the equilibrium from polymer to silacrown. It appears that there is some molecular rearrangement from polymer to silacrown during the course of distillation in the presence of transesterification catalysts that results from this preferential removal of the more volatile silacrowns from the reaction mixture.

The direct interaction of chloro-, amino-, and acyloxysilanes with polyethylene glycols can also lead to the desired products, but in significantly lower yield.

The silacrown ethers prepared in accordance with the present invention correspond to the general formula:

wherein:

$R^1$ and $R^2$ are organic radicals or hydrogen;
n is an integer between 4 and 10 inclusive.

Specific examples of the R groups are methyl, ethyl, benzyl, phenyl, cyclohexyl and phenethyl which may be utilized to alter solubility characteristics. Alkoxy, vinyl and aminoalkyl groups may be employed to enable coupling to a substrate. Within the scope of this invention, it is obvious that any R group that is compatible with the methods of synthesis cited, and which does not alter the crown structure, is acceptable.

The value of n is limited by the ability to recover the silacrown product by distillation during synthesis. For n values above 10, the silacrown is impossible to separate from the reaction mixture. The preferred values of n are 4–7.

The following Examples 1–4 demonstrate the synthesis of silacrowns.

EXAMPLE 1

VINYLMETHYLSILA-14-CROWN-5

A 250 ml single neck flask equipped with a magnetic stirrer and heating mantle is charged with 0.5 M (93 ml) of vinylmethyldiethoxysilane, 0.5 M (96 ml) of tetraethylene glycol and 0.5 ml of tetrabutyltitanate. The mixture was stirred at 50°–60° C. for 16 hours with a cold-finger distillation head in place. The pot temperature was increased to 85°–100° C. and about 50 ml of ethanol was removed. The mixture was then distilled under vacuum. The fraction boiling at 129°–131° C. at 0.5 mm was collected. Approximately 62 g of vinylmethylsila-14-crown-5 was isolated. The compound was identified by characteristic infrared absorption and organic mass spectroscopy. As expected, the compound did not exhibit a molecular ion, but exhibited (M—CH$_3$)$^+$ at 247 and (M—CH=CH$_2$)$^+$ at 235.

EXAMPLE 2

VINYLMETHYLSILA-17-CROWN-6

Under the same conditions described above, 37.4 ml of vinylmethyldiethyoxysilane, 46.6 g of pentaethylene glycol, 0.2 ml of tetraisopropyltitanate and 25 ml of toluene were charged into a 250 ml flask. Approximately 20 ml of ethanol was removed at atmospheric pressure. The product fraction was collected at 169°–172° C. at 0.3 mm. The yield was 36 g. The analysis was performed as above.

EXAMPLE 3

DIMETHYLSILA-17-CROWN-6 and DIMETHYLSILA-20-CROWN-7

Under conditions similar to those described in Example 1, 148.3 g of dimethyldimethoxysilane was combined with 300 g of a mixture of polyethylene glycols with an average molecular weight of 300. Two hundred and thirty grams of DIMETHYLSILA-17-CROWN-6, b.p. 169°–170° C. at 0.3 mm, and 45 g of DIMETHYLSILA-20-CROWN-7, b.p. 240°–244° C. at 0.2 mm, were obtained.

EXAMPLE 4

METHYOXYMETHYLSILA-17-CROWN-6

Under conditions analogous to Example 2, methyoxymethylsila-17-crown-6, b.p. 170°–173° C. at 3 mm, was obtained.

The following Tables I–III demonstrate the utility of the silacrowns as soluble phase transfer catalysts. The general regimen for the experiments was to combine 0.05 M of organic reactant with 0.10 M of inorganic reactant (neat or saturated aqueous solution), 25 ml of acetonitrile and 1 ml of silacrown, with agitation for 16 hours. Unless otherwise noted, the reactions were run at ambient temperature.

Table I demonstrates the substitution reaction of cyanide with benzyl bromide with and without silacrown-promoted catalysis. The table further gives a comparison with 18-crown-6 and decamethylcyclopentasiloxane (D$_5$). Reaction conditions and times were not optimized.

Table II demonstrates anion activation substitution reactions of halogens, pseudohalogens and organic anions. The reactions proceed readily under mild conditions.

Table III demonstrates the solid/liquid phase transfer catalysis of potassium cyanide substitution reactions.

Immobilized phase transfer catalysts are formed by incorporating methoxy silacrowns into a refluxing mixture of toluene and controlled pore glass. Example 5 describes the procedure employed to immobilize methoxymethylsila-17-crown-6. The resulting immobilized silacrown is depicted in FIG. 2.

EXAMPLE 5

IMMOBILIZATION OF METHOXYMETHYLSILA-17-CROWN-6

Controlled pore glass (80–120 mesh, 226 A, 99 m$^2$/g) was treated with 10–15% HCl overnight to induce silanol formation, washed with water and dried free of bulk water. A single neck flash was charged with 50 ml of a 2% solution of methoxymethyl-sila-17-crown-6 and 10 g of porous glass. The mixture was refluxed overnight. The treated beads were washed with toluene and dried.

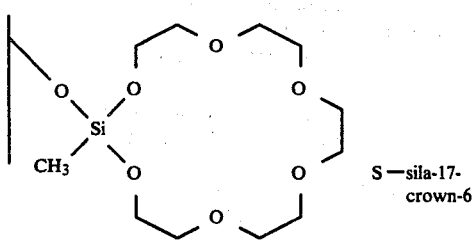

FIG. 2

S—sila-17-crown-6

— sila-17-crown-6 was used as a liquid/liquid phase transfer catalyst for various cyanide displacement reactions. The immobilized silacrown was added to a two-phase mixture containing concentrated aqueous potassium cyanide and a substrate dissolved in acetonitrile. The procedure for these experiments is described in Example 6; results appear in Table IV.

EXAMPLE 6
IMMOBILIZED PHASE TRANSFER CATALYST-PROMOTED POTASSIUM CYANIDE SUBSTITUTION

A concentrated aqueous solution of potassium cyanide was prepared containing 1 g of KCN in 2 ml of solution. 0.05 M of organic reactant was combined with 0.1 M of aqueous KCN and 2 g of silacrown treated porous glass. The reaction mixtures were stirred at 600–1000 rpm with a magnetic stirrer. Product conversion was determined by gas chromatography.

The present invention may be embodied in other specific forms without departing from the spirit or essential attributes thereof and, accordingly, reference should be made to the appended claims, rather than to the foregoing specification, as indicating the scope of the invention.

TABLE I
REACTIONS OF MCN WITH BENZYL BROMIDE

| CONDITIONS | REACTANT | CATALYST | TIME (HOURS) | YIELD |
|---|---|---|---|---|
| Solid/Liquid | KCN | — | 4 | 0% |
| Solid/Liquid | KCN | — | 48 | 54% |
| Solid/Liquid | NaCN | — | 4 | 0% |
| Liquid/Liquid | KCN | vinylmethylsila-17-crown-6 | 16 | 100% |
| Liquid/Liquid | KCN | sila-17-crown-6 | 16 | 100% |
| Solid/Liquid | KCN | 18-crown-6* | 6 | 100% |
| Solid/Liquid | KCN | D5** | 16 | 20% |
| Solid/Liquid | NaCN | sila-14-crown-5 | 16 | 100% |
| Solid/Liquid | KCN | sila-14-crown-5 | 4 | 3% |

Reactions at room temperature in acetonitrile
*Literature Values
**Decamethylcyclopentasiloxane

TABLE II
SILA-17-CROWN-6 CATALYZED REACTIONS OF BENZYL BROMIDE + KX

| REACTANT | PRODUCT | YIELD |
|---|---|---|
| KCN | Benzyl Cyanide | 100% |
| KOAc | Benzyl Acetate | 100% |
| KF | Benzyl Fluoride | 5% |
| KF at reflux 48 hours | Benzyl Fluoride | 55% |

Reaction after 16 hours at ambient temperature in acetonitrile with 0.13M silacrown

TABLE III
SILACROWN SOLID/LIQUID PHASE TRANSFER CATALYSIS OF POTASSIUM CYANIDE SUBSTITUTIONS

| REACTANT | CATALYST | TIME (HOURS) | YIELD |
|---|---|---|---|
| Octyl Bromide | sila-17-crown-6 | 48 | 63% |
| Hexyl Bromide | 18-crown-6* | 40 at reflux | 100% |
| Benzyl Bromide | sila-17-crown-6 | 16 | 100% |
| Benzyl Chloride | sila-17-crown-6 | 16 | 100% |
| Allyl Bromide | sila-14-crown-5 | 16 | 0% |
| Benzyl Chloride | — | 48 | 29% |
| Benzyl Chloride | —* | 75 | 25% |
| Benzyl Chloride | 18-crown-6* | 1 | 99% |
| Allyl Bromide | sila-17-crown-6 | 16 | 74%** |
| Allyl Bromide | — | 16 | 0% |

Reactions at room temperature in acetonitrile
*Literature Value
**Mixtures of allyl cyanide and crotononitrile

TABLE IV
IMMOBILIZED PHASE TRANSFER CATALYST-PROMOTED POTASSIUM SUBSTITUTION

| CATALYST | REACTANT | TIME (HOURS) | PRODUCT | YIELD |
|---|---|---|---|---|
| S - sila-17-crown-6 | allyl bromide | 16 | allyl cyanide | 45% |
|  |  |  | crotononitrile | 55% |
| S - sila-17-crown-6 | benzyl bromide | 25 | benzyl cyanide | 100% |
| S - sila-17-crown-6 | benzyl chloride | 16 | benzyl cyanide | 97% |

S - indicates support bound

I claim:
1. Compounds of the structure:

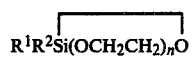

$$R^1R^2Si(OCH_2CH_2)_nO$$

wherein n is an integer from 4 to 10 inclusive, and $R^1$ and $R^2$ are selected from the group consisting of alkyl, unsaturated alkyl, alkoxy, aryl and hydrogen.

2. Compounds according to claim 1 wherein n is 4, $R^1$ is methyl, and $R^2$ is selected from the group consisting of methyl, vinyl and phenyl.

3. Compounds according to claim 1 wherein n is 5, $R^1$ is methyl, and $R^2$ is selected from the group consisting of methyl, vinyl and methoxy.

4. A compound according to claim 1 wherein n is 6 and $R^1$ and $R^2$ are both methyl.

5. A method for producing silacrown ethers by a transesterification reaction between a polyethylene glycol having the general formula:

$$HO(CH_2CH_2O)_nH$$

where n is an integer from 4 to 10 inclusive, and a silane having the general formula:

$$R^1R^2Si(Y)_2$$

in the presence of a catalyst which promotes cyclization over polymerization, wherein Y is selected from the group consisting of alkoxy, acyloxy, amino and chloro, and $R^1$ and $R^2$ are selected from the group consisting of alkyl, unsaturated alkyl, alkoxy, aryl and hydrogen.

6. A method according to claim 5 wherein the reaction is carried out in the presence of a high-boiling solvent.

7. A method according to claim 5 wherein the product is removed from the reaction mixture by distillation.

8. A method according to claim 5 wherein the silane is vinylmethyldiethoxysilane and the polyethylene glycol is selected from the group consisting of tetraethylene glycol and pentaethylene glycol.

9. A method according to claim 5 wherein dimethyldimethoxysilane is reacted with a mixture of polyethylene glycols.

10. A method according to claim 5 wherein methoxymethyldiethoxysilane is reacted with pentaethylene glycol.

11. Immobilized silacrown ethers formed by the reaction of siliceous materials and silicrown ethers.

12. Immobilized silacrown ethers according to claim 11 formed by the addition of a methoxysilacrown to a refluxing mixture of toluene and controlled pore glass.

* * * * *